(12) United States Patent
Ross et al.

(10) Patent No.: US 7,627,083 B2
(45) Date of Patent: Dec. 1, 2009

(54) METHOD AND APPARATUS FOR AUTOMATED, DIGITAL, RADIOGRAPHIC INSPECTION OF AEROSPACE PARTS

(75) Inventors: Michael Thomas Ross, Vandalia, OH (US); Samir Anjelly, Islip, NY (US); James Harcourt Brim, Suwanee, GA (US); Robert Louis Lukasik, Lawrenceville, GA (US)

(73) Assignee: VJ Technologies, Bohemia, NY (US)

( * ) Notice: Subject to any disclaimer, the term of this patent is extended or adjusted under 35 U.S.C. 154(b) by 0 days.

(21) Appl. No.: 12/075,708

(22) Filed: Mar. 12, 2008

(65) Prior Publication Data

US 2008/0226028 A1 Sep. 18, 2008

Related U.S. Application Data

(60) Provisional application No. 60/906,579, filed on Mar. 13, 2007.

(51) Int. Cl.
*G01N 23/02* (2006.01)
(52) U.S. Cl. .............................. 378/58; 378/62; 378/196
(58) Field of Classification Search ............... 378/4–20, 378/58–60, 62, 167, 189, 193–198
See application file for complete search history.

(56) References Cited

U.S. PATENT DOCUMENTS

| 7,170,972 B2 * | 1/2007 | Altman ........................ 378/62 |
| 7,500,782 B2 * | 3/2009 | Klingenbeck-Regn et al. .......................... 378/197 |

* cited by examiner

*Primary Examiner*—Jurie Yun
(74) *Attorney, Agent, or Firm*—Kiran Malhotra

(57) ABSTRACT

A system and method for automatic digital radiographic inspection of round aerospace parts (18) and irregularly shaped aerospace parts (19) includes a radiation source (14) and a radiation detector (16) located on opposite sides of the aerospace part to receive the radiation from the radiation source. In operation the radiation source and the radiation detector are manipulated by a robot (10) in six independent axes of motion. The aerospace part is rotated by a part manipulator (20) to provide the seventh axis of motion and the aerospace part is tilted to provide the eighth axis of motion. This allows every portion of the aerospace part to be examined. The radiation detector converts the impinging radiation into electrical signals and the system generates the radiographic images and archives these images.

19 Claims, 6 Drawing Sheets

50

METHOD AND APPARATUS FOR AUTOMATED, DIGITAL, RADIOGRAPHIC INSPECTION OF AEROSPACE PARTS

CROSS-REFERENCE TO RELATED APPLICATIONS

This application claims the benefit of provisional patent application Ser. No. 60/906,579, filed 2007 Mar. 13 by the present inventors.

FEDERAL SPONSORED RESEARCH

Not Applicable

SEQUENCE LISTING OR PROGRAM

Not Applicable

BACKGROUND OF THE INVENTION

Field of Invention

This invention relates to automatic radiographic inspection and automated image acquisition of aerospace engine parts that are hollow and round such as engine fan frames, combustion housings and stators as well as irregularly shaped aerospace parts such as turbine blades. The round parts typically range from two to six feet in diameter and the irregular parts are usually smaller with complex geometries and undercuts.

Aerospace engine parts require non destructive inspection in order to ensure that the product is safe for use in a jet engine. These parts need to be free of all flaws; such as porosity flaws and other internal voids remaining from the aerospace part manufacturing process to ensure that the parts are safe for use in the aircraft.

These flaws are internal and are detectable only by radiographic techniques such as x-ray inspection.

In order to completely inspect these parts there may be multiple views (in the hundreds) required in order to provide for 100 percent inspection of each portion of the aerospace part.

The current state of the art involves putting the aerospace part into a radiation shielded x-ray vault and then imaging the part in a manual and slow fashion. Only a single area covering approximately 14"×17" of a given part can be x-rayed at a single time. The aerospace part is placed in the vault with a single piece of film located in a specific position. The vault is closed and the film exposed to the x-ray; the vault is opened the film removed and the part manipulated to allow for the next image. A typical operation will complete only six to ten images in an hour. Because there may be hundreds of images required the current state of the art is time consuming and expensive. After the film is removed the film needs to be taken to a dark room and further processed to develop the image and then read against a light box. This manual process takes approximately ten minutes per image adding to time and cost of the process as it is currently practiced. The inspectors enter and exit the vault to set up and remove every exposure.

Accordingly, there is a need for a method and a system to automate the process and to ensure reliable and efficient inspection of every portion of the aerospace part as is provided by this invention.

BRIEF SUMMARY OF THE INVENTION

The above mentioned need is met by the present invention, which according to one aspect provides a system for automatic digital radiographic inspection of aerospace parts; including a supporting means for the radiation source and the radiation detector such that the radiation source and the radiation detector are located on opposite sides of the wall of the round aerospace part. Means are provided to pivotably hold the aerospace part and a computer controls the movement of the supporting means and the holding means to provide seven independent axes of motion. Means are provided to tilt the aerospace part to provide an eighth independent axis of motion. An imaging unit is provided to receive the data from the radiation detector.

According to another aspect of the invention, a method for automatic digital radiographic inspection of aerospace parts includes providing a radiation source and radiation detector mounted on a c-arm support such that the radiation source and the radiation detector are situated on the opposite sides of the wall of the aerospace part, providing robot manipulation of the c-arm in six independent axes of movement; providing a seventh independent axes of motion by rotating the aerospace part; providing an eighth independent axes of motion via a tilting mechanism; subjecting the robot to teach-learn sequence using pendant control; manipulating the c-arm and the aerospace part in eight independent axes of motion such that every portion of the aerospace part is inspected and collecting the digital signals from the radiation detector.

According to another aspect of the invention a system of automatic digital inspection of aerospace parts includes: a radiation source attached to one prong of a c-arm and a radiation detector situated directly opposite on the other prong of the c-arm; a robot with six independent axes of motion attached to the c-arm; a part manipulator used to mount the aerospace part as well as rotate the aerospace part in the seventh independent axis of motion; a tilt mechanism to tilt the part manipulator and provide the eight independent axis if motion; a computer to control the movement of the robot and the part manipulator; and means for collect the image data from the radiation detector.

DRAWINGS

Figures

DRAWINGS

Figure 1:
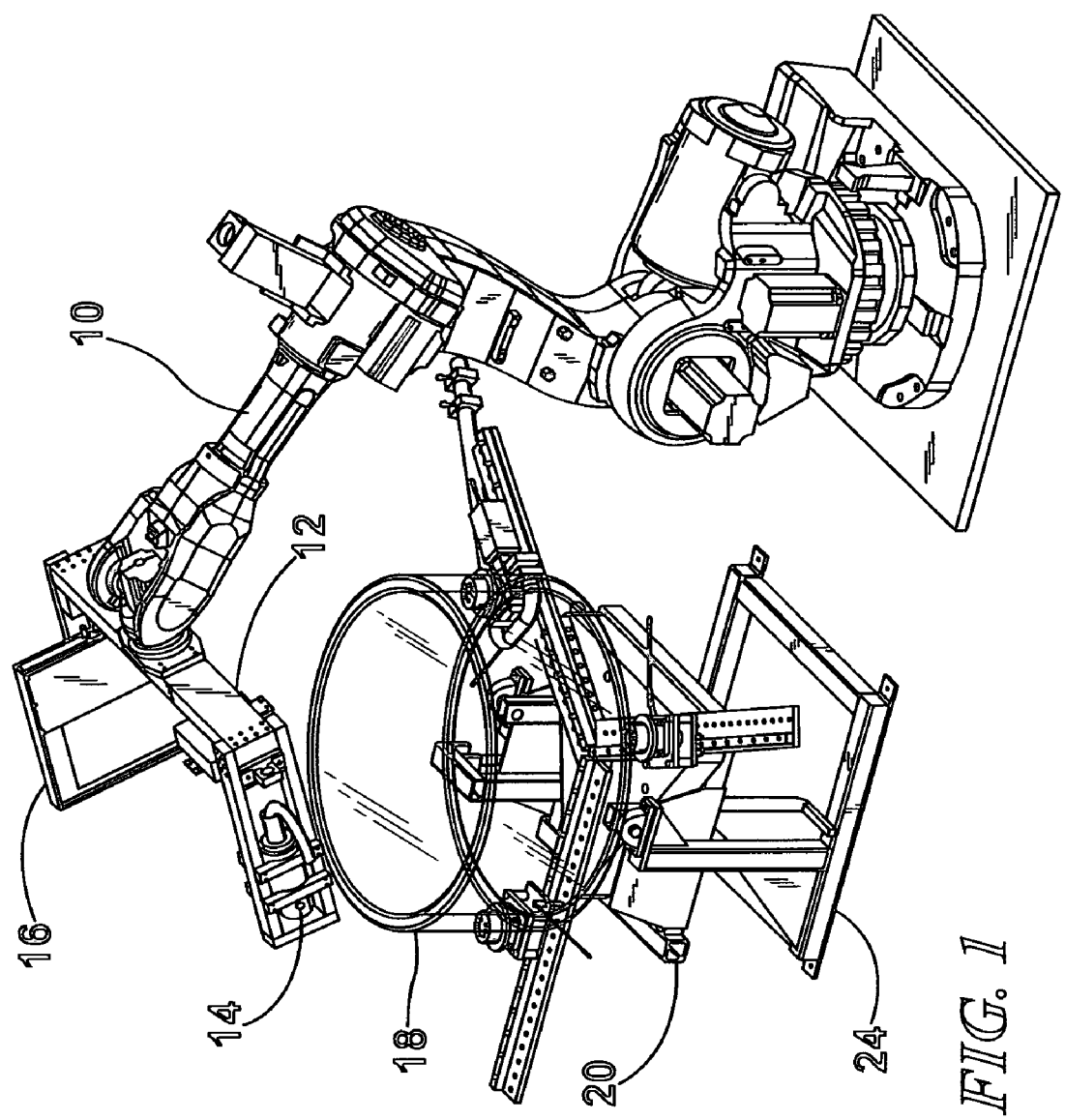
FIG. 1 shows a perspective view of the main components of the system including the robot, c-arm, part manipulator, the aerospace part to be examined and the computer station.
Figure 1:
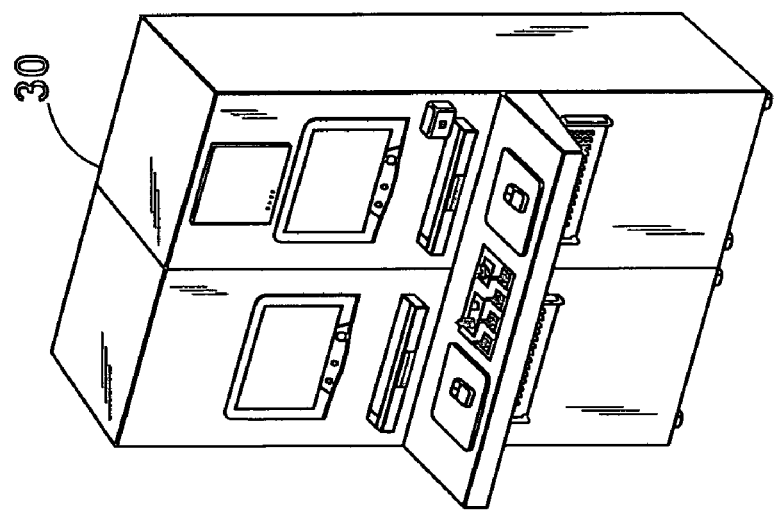

Reference Numerals 10 robot
12 c-arm
14 x-ray Source
16 x-ray Detector
18 large round part
19 small parts
20 part manipulator
22 three jaw chuck
24 raised base
26a, 26b, 26c arms
27a, 27b, 27c set of rollers
28 fixture
29 servo motor
30 computer station
32 tilt control
40 system for automated radiographic inspection of large round parts.
50 system for automated radiographic inspection of small parts.

In the drawings identical reference numerals denote the same elements throughout the various views.

DETAILED DESCRIPTION

FIG. 1—Preferred Embodiment

Figure 2:
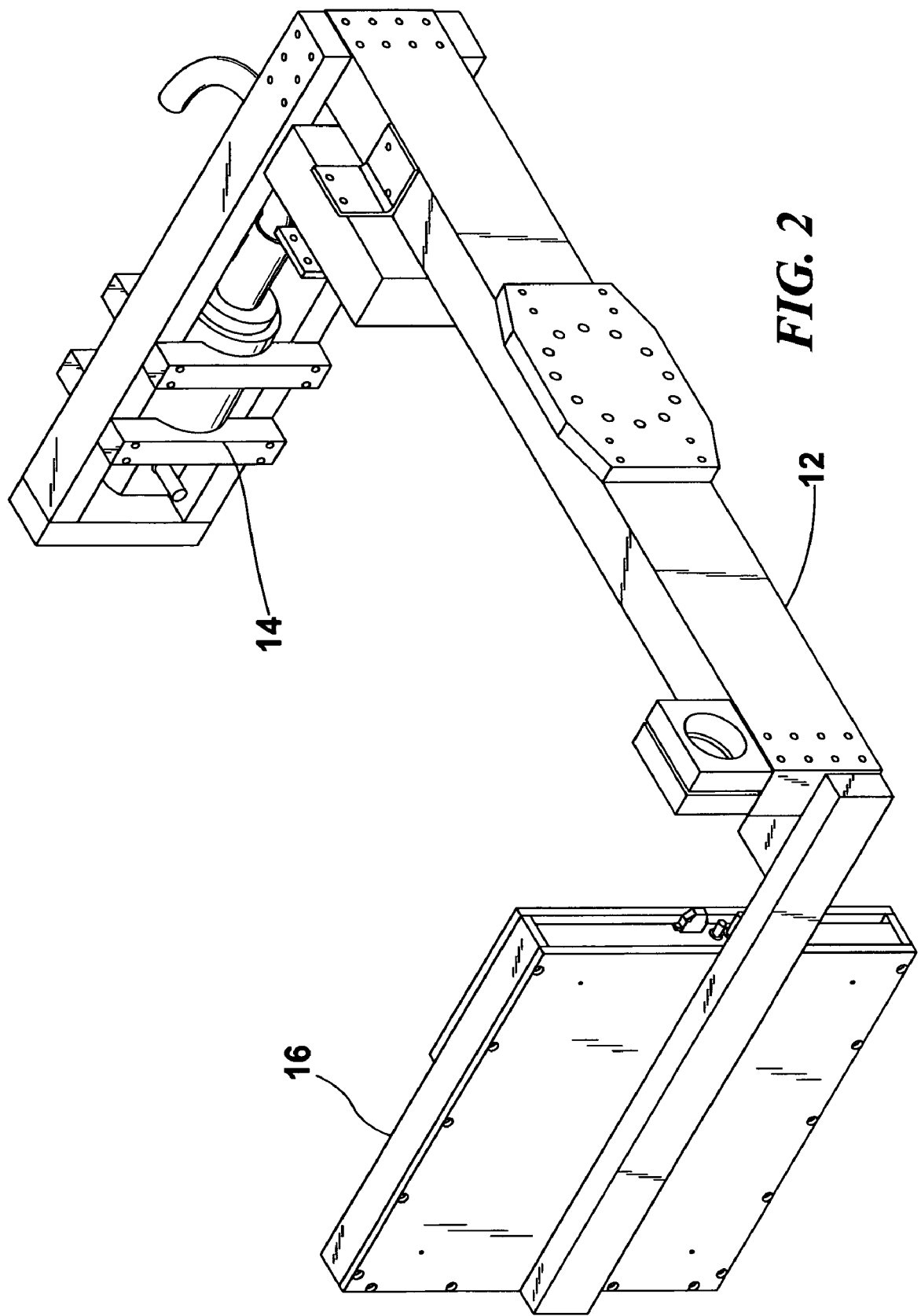
FIG. 2 shows a perspective view of the c-arm with the x-ray source and detector mounted on the two arms.

A preferred embodiment of the invention to hold; manipulate and x-ray the part is shown in FIG. 1. It shows a perspective view of the robot 10, c-arm 12, x-ray source 14, x-ray detector 16 and the part manipulator 20 holding the large round part 18 to be examined. The robot 10 is a conventional six-axis robot such as ABB™ Robot Model 660-225/2.55 that has a load capability to allow for manipulation of the c-arm 12 at full extension. The robot 10 is used to manipulate the c-arm 12 in the six primary axes of movement. The x-ray source 14 is mounted on one branch of the c-arm via conventional mechanical clamping device and the x-ray detector 16 is connected to the opposite branch of the c-arm 12 with a conventional mechanical clamping device. FIGS. 1 & 2 show the positioning in the c-arm 12 such that the radiation emitted by the x-ray source 14 irradiates the large part 18 or the small parts 19 held in the part manipulator 20 and then impinges on the x-ray detector 16. The opening of the C-arm 12 is adjustable to create a separation between the x-ray source 14 and the x-ray detector 16. A skilled x-ray technician can make the adjustment to create the desired sharpness of the x-ray image. Typically, a distance between 46 inches (1150 mm) and 60 inches (1524 mm) is used.

The x-ray source 14 in the preferred embodiment is a typical fractional focus x-ray source capable of an energy level necessary to penetrate the wall of the aerospace part such as Comet™ MXR-225/21 that is a 225 kV tube with dual focal spots and an overall power rating of 1200 W. This source is interchangeable and the system can be configured with both larger energy sources for thicker parts and materials of greater density as well as micro-focus sources for fine resolution inspection. The detector 16 is a typical amorphous silicon digital panel x-ray detector such as Thales™ Model Flash 23. It is capable of converting the photons received through the inspection part and, through the software and associated electronic hardware, converting the density of those photons into an image which can be inspected by the operator.

Figure 3:
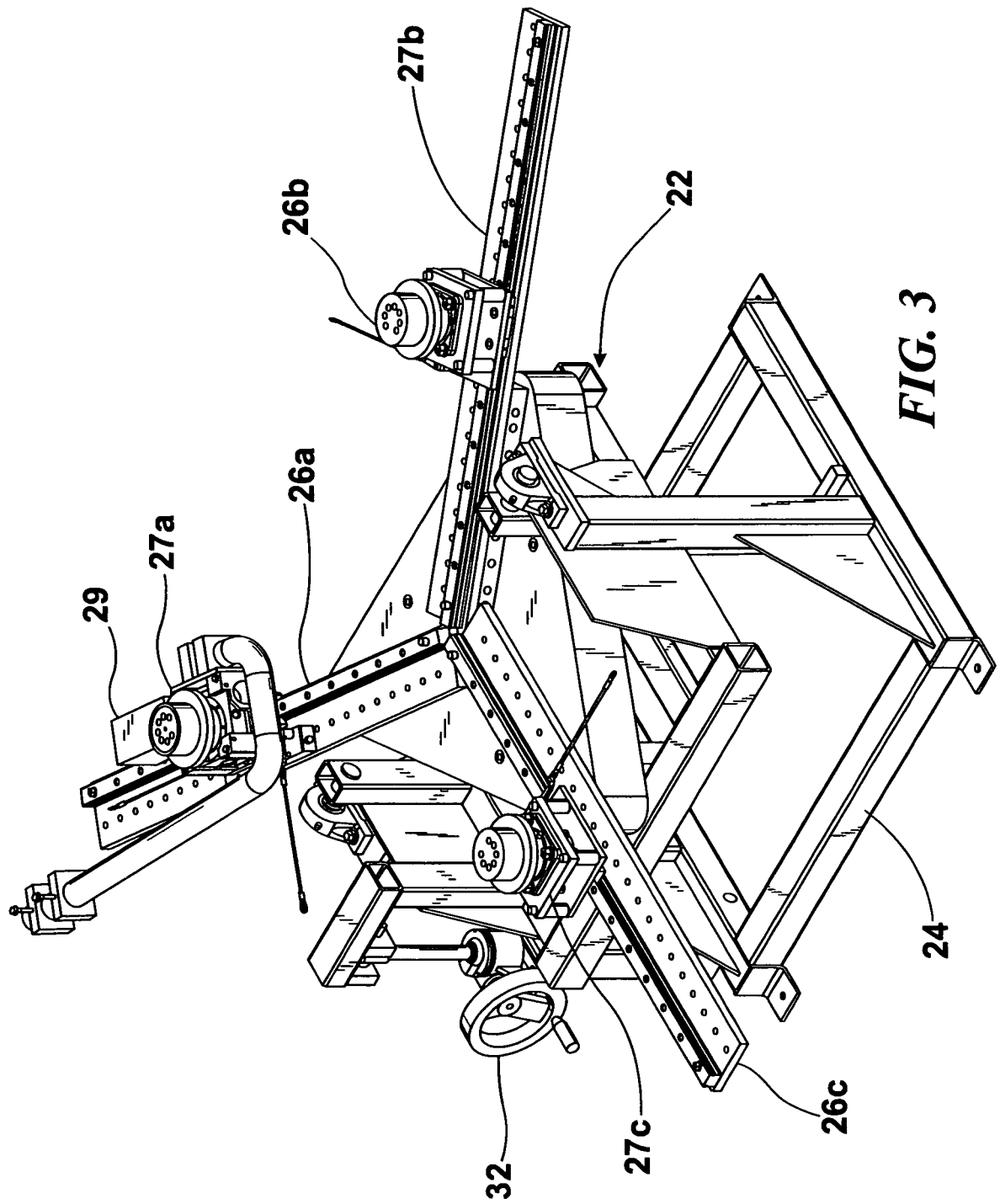
FIG. 3 shows a perspective view of the part manipulator for large round parts.

FIG. 3 shows the part manipulator 20 that provides the seventh rotational axis of movement. It utilizes a three jaw chuck 22 attached to a raised base 24. The three jaw chuck 22 holds three arms 26a, 26b and 26c each equipped with a set of rollers 27a, 27b and 27c. The rollers are set on springs. The large round part 18 to be inspected is placed on top of the sets of rollers 27a, 27b and 27c and clamped by jaw chuck 22. Thereby, the large round part 18 is securely held in the part manipulator 20. Large round parts typically range in diameter from 24 inches to 72 inches. Parts that are smaller than 24 inches or parts that are non-circular in shape will require special fixtures whose design will depend on the particular shape of the part to be examined.

A conventional servo motor 29 such as Baldor™ operates roller 27a and is controlled by the computer station 30 via robot 10. The base of the part manipulator 20 can be tilted with tilt control 32. The tilt control 32 allows for manual screw based tilting of the inspection base. The tilt control 32 provides the eight independent axis and permits inspection of areas of the large part 18 that otherwise would be inaccessible. By tilting the inspection base the system is capable of allowing complex angles of entry for the c-arm and inspection devices. The base is tilted with a typical industrial wheel mounted to a screw drive on a small gearbox.

Figure 4:
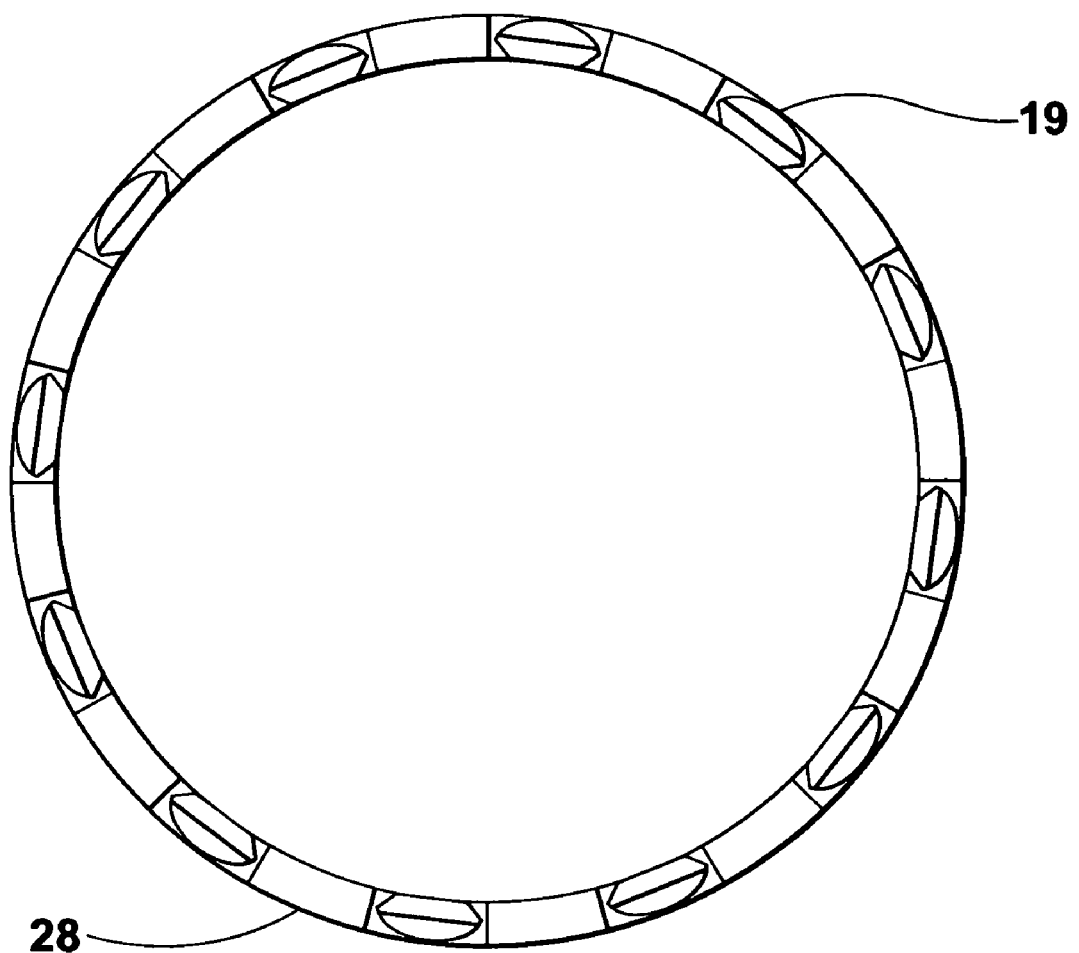
FIG. 4 shows the top view and the side view of the fixture that is mounted on the part manipulator for inspection of smaller parts.
Figure 4:
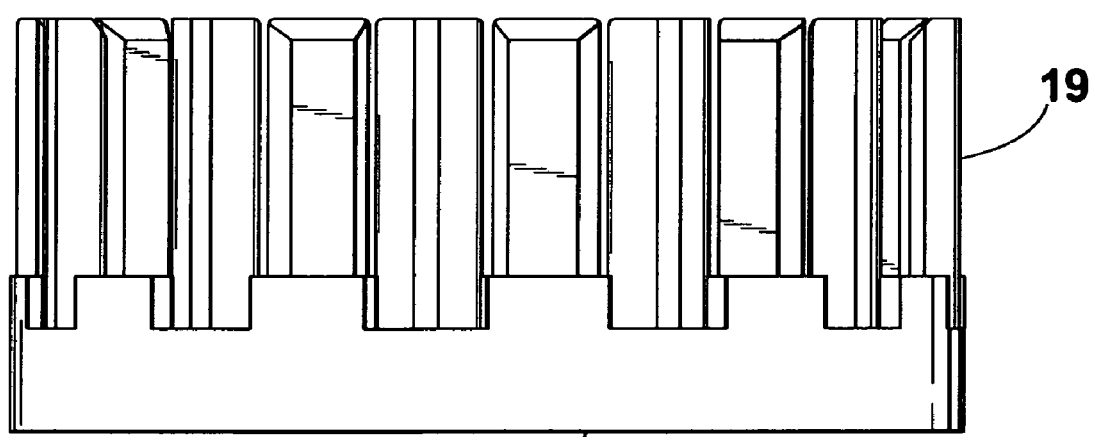
Figure 5:
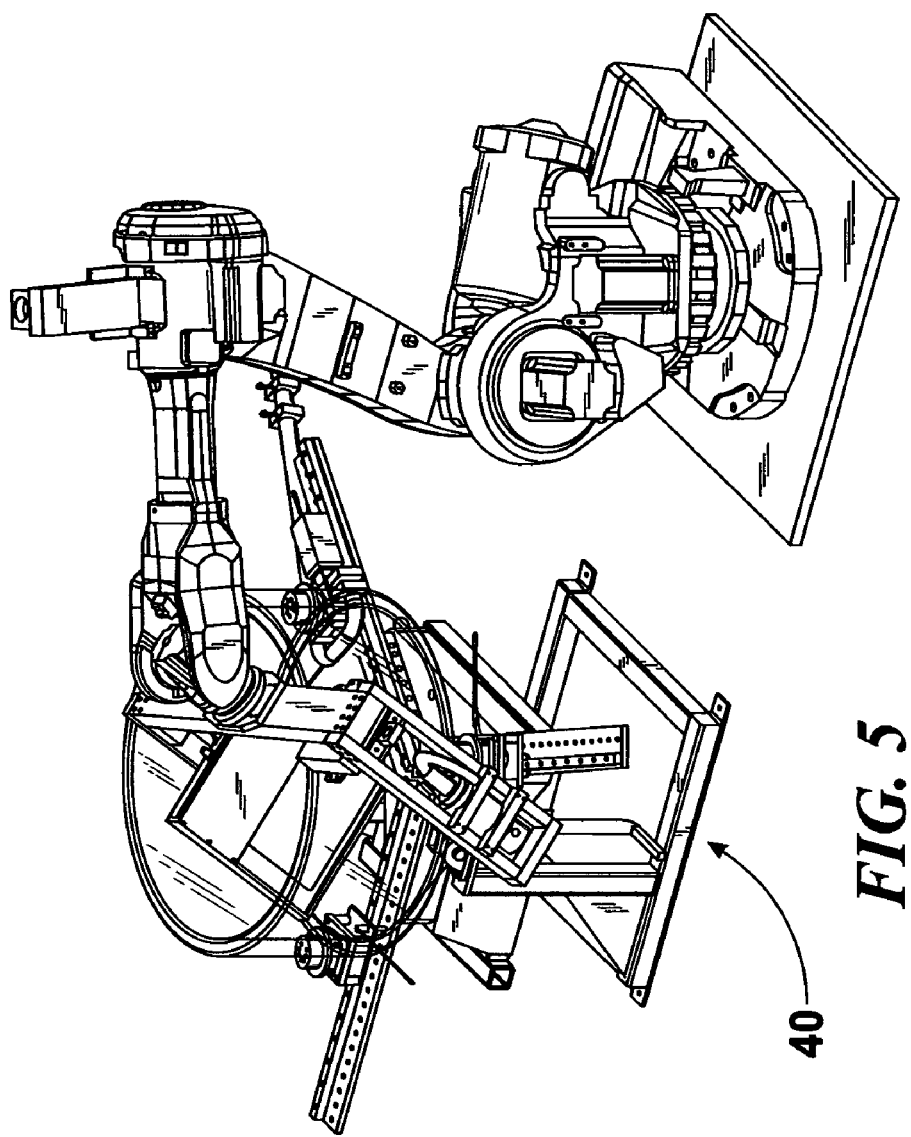
FIG. 5 shows the complete system for automated digital radiographic inspection of large round aeronautical parts.
Figure 5:
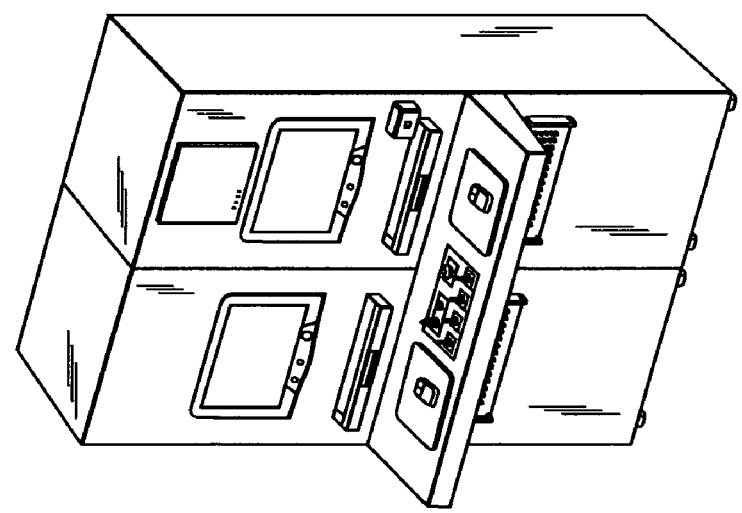
Figure 6:
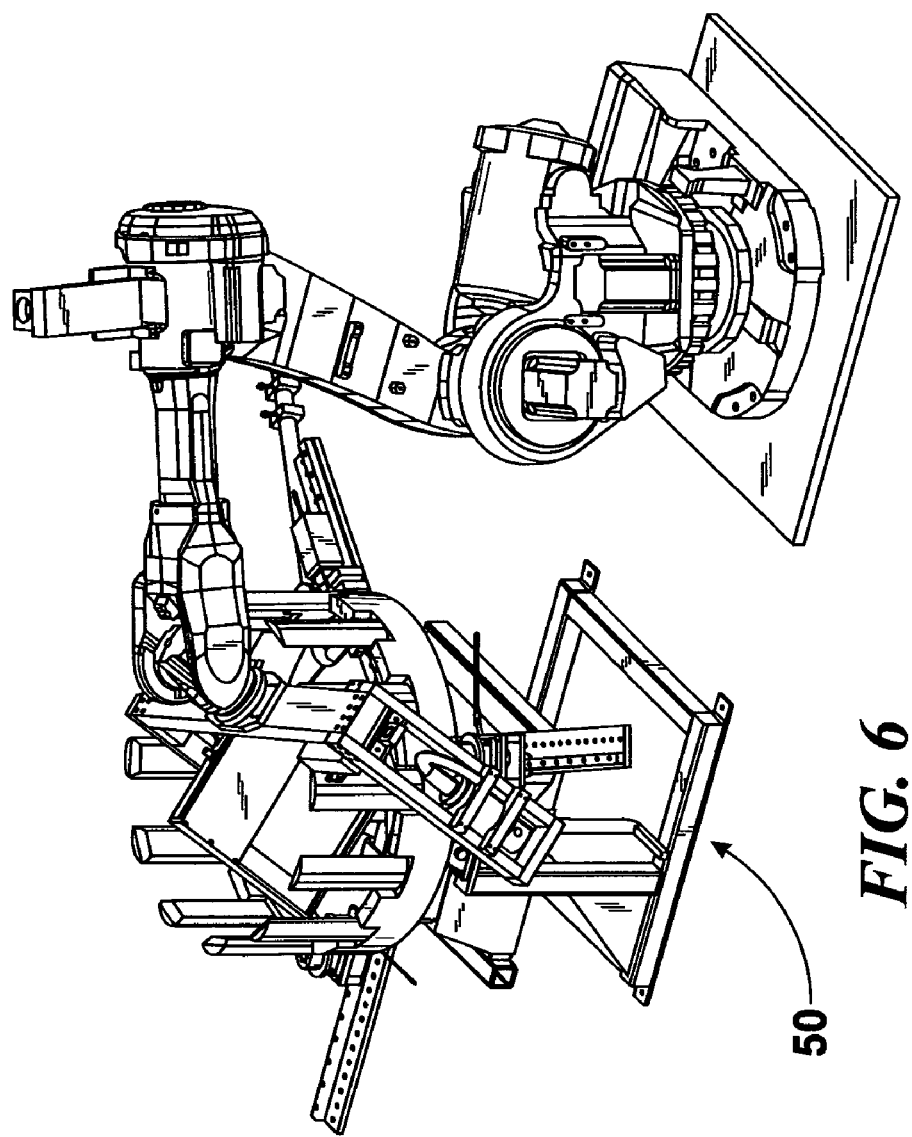
FIG. 6 shows the complete system for automated digital radiographic inspection of small parts and non round parts that utilizes a fixture to hold these parts.
Figure 6:
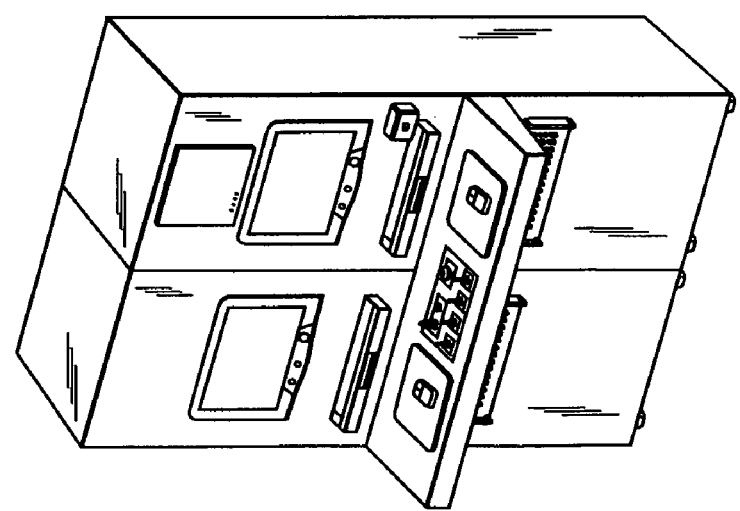

FIG. 4 shows the part manipulator 20 adapted by using a fixture 28 capable of holding a multiple of small parts 19. The fixture 28 is attached to the part manipulator 20 in the same manner as used for the large part 18.

Operation

The system shown in FIG. 1 enables automation of X-Ray inspection in a single step capturing x-ray images of every portion of the part to be inspected. The system is comprised of the robot 10 holding a c-arm 12 which carries the X-ray source 14 and the x-ray detector 16. The robot manipulates the c-arm to position the x-ray source 14 and the x-ray detector 16 in various positions around the large round part 18. The x-ray source 14 is positioned by the c-arm outside the large round part to be inspected 18 and the x-ray detector 16 is positioned by the c-arm inside the large round part 18 such that the x-ray radiation can pass through the large part 18 and strike the detector 16. The part manipulator 20 holds the large round part to be inspected 18 and is controlled by the robot 10 to allow for a total of eight independent axes. Six of the axes are provided by the robot 10; the seventh axis is the rotation axis provided by the part manipulator 20 and the eighth axis is provided by the tilt control 32. The system is programmed such that six axes provided by the robot 10 works in conjunction with the seventh axis provided by the part manipulator 20. This combination of the six axes provided by the robot 10 with the seventh axis provided by the part manipulator 20 creates the unique ability in combination with the computer software program (not described here) to create a complete inspection sequence that moves the c-arm 6 around the large round part 18 capturing x-ray images of every portion of the part. The part manipulator 20 operates in a manner intended to augment the part inspection capabilities of the system. As described earlier, the part manipulator 20 utilizes a three jaw chuck 22 attached to a raised base 24. The three jaw chuck 22 holds three arms 26a, 26b and 26c each equipped with a set of rollers 27a, 27b and 27c. The rollers are set on springs. The large round part 18 to be inspected is placed on top of the sets of rollers 27a, 27b and 27c and clamped by jaw chuck 22. Thereby, the large part 18 to be examined is securely held in the part manipulator 20. Roller 27a is powered by the motor 29, which is controlled by the robot 10 and allows the large part 18 to be rotated while the robot is moving the c-arm 12 around it. The raised base 24 of the part manipulator 20 is capable of being tilted using tilt control 32, which allows the large round part to be examined in segments that would otherwise have been inaccessible to the radiation because of limitations of movement of the robot 10.

The operation begins with the operator establishing an initial inspection position using the robot 10 that is operated via the computer station 30. The large part to be inspected 18 is loaded on the part manipulator 20 and the robot is subjected to a teach-learn sequence using a pendant control. The use of teach-learn and pendant control is common in robotics and easily understood by a person skilled in the art. Once the sequence is established the robot 10 sends the information to the computer station 30 where the software develops a program for inspection of the large part 18. The program used controls the movement of the robot 10, positions the c-arm 12 and controls the movement of the part manipulator 20. The x-ray exposure for each position of the part manipulator 20 as it is moved through the inspection sequence is controlled by the software program operating the computer station 30. The x-rays emitted by the x-ray source 14 irradiate the large round part 18 and then is measured by the x-ray detector 16. The x-ray exposures are controlled by the software program operating in the computer station that allows automated control of the output parameters such as kV and mA of the x-ray source 14 and the control parameters such as frames of averaging, dwell times and other exposure parameters of the x-ray detector 16. Image data output from the x-ray detector are fed to the computer station 30, which processes these signals and displays them as a computer image on its monitor for the operator to inspect for any defects. Once the program is established a completely repeatable inspection is conducted on the large round part 18 and a series of programmed images are presented to the operator at the computer station 30.

The computer station 30 is capable of providing many other functions (not covered here) that allows the operator to view each image in a controlled and cataloged fashion that meets the stringent requirements of the aerospace manufacturing community. It also allows for digital archiving of the images.

In addition to being able to inspect large round part 18, the system is capable of inspecting smaller components such as turbine blades. A number of the small parts 19 are loaded onto the fixture 28 that is itself mounted on the part manipulator 20. The part manipulator is programmed using the previously mentioned teach-learn process to rotate the parts in front of the c-arm 12 in order to create x-ray images of each of the small parts 19 that have been loaded on to the fixture 28. The fixture design is dependant on the shape and size of the small part 19 to be examined. At the same time the c-arm 12 is moved by the robot 10 around the smaller parts in order to obtain a variety of x-ray views of these parts.

The robot 10 is used to manipulate the c-arm 12 in the six primary axes of movement. The part manipulator 20 provides the seventh rotational axis of movement and the tilt control 32 provides the eight independent axis and permits inspection of areas of the small parts 19 with undercuts that otherwise would be inaccessible.

Using the teach and learn mode via manipulation of the c-arm 12; the part manipulator 20 and the tilt control 32, the operator is able to complete the entire inspection of a the aerospace parts with a single load into the x-ray vault. The software program used (not described here) allows the computer station 30 to program every step of the operation from the positioning of the robot 10 to the control settings of the x-ray source 14 to the image settings of the x-ray detector 16 to the digital storage of these images. Once the teach and learn mode is completed the software program automates the process for rapid inspection that is completely repeatable.

The radiation source 14 is preferably, but not necessarily a standard X-ray such as Comet™ MXR-225/21, but alternative radiation sources such as an isotopic radiation source producing gamma rays could be used as well.

DESCRIPTION AND OPERATION OF ALTERNATIVE EMBODIMENTS

While the system in the preferred embodiment is equipped with a 225 kV energy level, the c-arm 6 is designed to accommodate up to 450 kV tubes and tubes as small as 130 kV micro-focus tubes. The current system design with a digital panel x-ray detector 16 can also be modified to accommodate both different sizes and types of digital flat panels as well as, linear diode arrays and other x-ray detection devices which can be mounted on the c-arm 6. The detector 16 in the preferred embodiment is a typical amorphous silicon digital panel x-ray detector, but it can be any means that is capable of processing radiation emitted by the radiation source 14 into a viewable image. It is preferred that that the radiation detector 16 be of the type that converts impinging radiation into an electric output signal although x-ray film could also be used. The preferred embodiment for manipulating parts 18 and 19 as described above uses the robot 10 to provide the six independent axes. Another method to provide the six axes of independence would be to build a mechanical manipulator held by a device such as a crane. It would be clear to a person skilled in the art to design such a device to provide a similar function as provided by the robot 10. It is also possible to use a different type of motor or a mechanical device to rotate the part manipulator 20 that provides the seventh independent axis. It is also possible to provide a motorized means for operating the tilt control 32 rather than the manually operated mechanical control showed in the preferred embodiment.

The foregoing has described a method and apparatus for digital radiographic inspection of aerospace parts that permits automated x-ray inspection in a single step capturing x-ray images of every portion of the part to be inspected without using the multi step process as described previously in the Background section. While specific embodiments of the present invention have been described, it will be apparent to those skilled in the art that various modifications thereto can be made without departing from the scope of the invention as defined in the claims below.

What is claimed is:

1. A system for automated, digital radiographic inspection of a round aerospace part, said system comprising:
   (a) a radiation source and radiation detector relatively situated on opposite sides of a wall of said round aerospace part;
   (b) supporting means for said radiation source and said radiation detector with opening on one end, the size of said opening being defined by the thickness of said wall of said round aerospace part;
   (c) first positioning means for six axes independent movement of said supporting means;
   (d) second positioning means for pivotably holding said round aerospace part and providing a seventh independent axis of movement;
   (e) third positioning means to tilt said second positioning means to provide an eighth independent axis of movement;

(f) computer for controlling said first and second positioning means said computer causing said supporting means to move around said round aerospace part in a predetermined sequence and (g) imaging unit that receives data signals from said radiation detector, whereby all segments of said round aerospace part via eight independent axes of movement are inspected and digital images of said aerospace part are created.

2. The system of claim 1 wherein said radiation source is a fractional focus x-ray source.

3. The system of claim 1 wherein said radiation detector is an amorphous silicon digital panel x-ray detector.

4. The system of claim 1 wherein said supporting means is a c-arm.

5. The system of claim 4 wherein said first positioning means is a robot whereby said c-arm is manipulated in said six axes of independent movement.

6. The system of claim 1 wherein said second positioning means is a part manipulator that comprises a three jaw chuck attached to a raised base and three arms mounted on said three jaw chuck, each of said three arms equipped with spring supported rollers whereby said aerospace part is fixed and capable of rotation in said seventh independent axis of movement.

7. The system of claim 1 wherein said third positioning means is a manual screw based tilt mechanism for said second positioning means whereby said aerospace part is tilted to provide said eighth independent axis of movement.

8. The system of claim 1 further comprising a fixture designed for non round aerospace part that is mounted on said part manipulator.

9. The system of claim 1 further comprising means for archiving of said digital images.

10. A method of automatic digital radiographic inspection of a round aerospace part comprising:
（a) providing a radiation source and a radiation detector relatively situated on a c-arm support on opposite sides of a wall of said round aerospace part;
(b) providing a robot to manipulate said c-arm in six independent axes of motion;
(c) providing a seventh independent axis of motion via rotary manipulation means of said aerospace part;
(d) providing an eighth independent axis of motion of said round aerospace part via a tilting mechanism;
(e) subjecting said robot to a teach-learn sequence using pendant control;
(f) causing said radiation source and said detector via computer control to move in the seven independent axes of motion and providing a tilt mechanism for the eighth independent axis of motion so that every segment of said round aerospace part is digitally inspected, whereby all portions of said aerospace part are automatically and digitally inspected.

11. The method of claim 10 further comprising collecting digital signals from said detector and digitally storing said digital signals.

12. The method of claim 10 further comprising: providing a fixture that is mounted on said rotary manipulation means, said fixture designed to hold non round aerospace parts.

13. A system for automated, digital radiographic inspection of a round aerospace part comprising:
(a) a radiation source attached to one prong of a c-arm and a radiation detector attached to a facing prong of said c-arm such that said radiation detector is fixed directly opposite to said radiation source;
(b) a robot with six independent axes of motion attached to said c-arm;
(c) a part manipulator that comprises a three jaw chuck attached to a raised base and three arms mounted on said three jaw chuck, each of said three arms equipped with spring supported rollers whereby said large round aerospace part is fixed and capable of rotation in a seventh independent axis of motion;
(d) a means for controlling said six independent axes of motion and said seventh independent axis of motion;
(e) a tilt mechanism to control an eighth independent axis of motion, whereby all segments of said round aerospace part via eight independent axes of motion are irradiated.

14. The system of claim 13 wherein the radiation source is a fractional focus x-ray source.

15. The system of claim 13 where the radiation detector is an amorphous digital silicon panel x-ray detector.

16. The system of claim 13 wherein said means for controlling said six independent axes of motion and said seventh independent axis of motion is a computer station.

17. The system of claim 13 with means to collect image data output from said radiation detector and display said data output on a computer screen as an x-ray image of said round aerospace part that is inspected for defects in said round aerospace part.

18. The system of claim 13 further comprising a fixture designed for non round aerospace parts that is mounted on said part manipulator.

19. The system of claim 13 further comprising means for archiving x-ray images.

* * * * *